United States Patent [19]

Niskin

[11] 4,302,974
[45] Dec. 1, 1981

[54] WATER SAMPLING DEVICE

[76] Inventor: Shale J. Niskin, 3415 Chase Ave., Miami Beach, Fla. 33140

[21] Appl. No.: 116,755

[22] Filed: Jan. 30, 1980

[51] Int. Cl.³ .............................................. G01N 1/12
[52] U.S. Cl. ................................................. 73/864.62
[58] Field of Search ........................ 73/425.4 R, 425.6

[56] References Cited

U.S. PATENT DOCUMENTS

| | | | |
|---|---|---|---|
| 3,176,517 | 4/1965 | Chelminski | 73/425.4 R |
| 3,242,740 | 3/1966 | Niskin | 73/425.4 R |
| 3,489,012 | 1/1970 | Niskin | 73/425.4 R |

Primary Examiner—S. Clement Swisher
Attorney, Agent, or Firm—William A. Newton

[57] ABSTRACT

Disclosed is a water sampling device having a pliable container, a pair of rods attached to opposed sides of an opening formed in the container, a clutch assembly having a rotatable outer member and a rotatable core member with said rods attached thereto, a pull-down spring for urging the wing members to descend down the tubular member so as to unroll the pre-rolled container to expose the opening, a pair of wing members slidably mounted on a tubular member and operative to spread apart the sides of the initially deflated container, and a wind-up spring for rotating the rods to roll up and reseal the container.

12 Claims, 22 Drawing Figures

WATER SAMPLING DEVICE

FIELD OF THE INVENTION

The present invention relates to devices for obtaining water samples from the ocean and other bodies of water.

DESCRIPTION OF THE PRIOR ART

Various types of water sampling devices are known in the art, as discussed in U.S. Pat. No. 3,242,740 to Niskin. The present invention is an improvement on the type disclosed in said U.S. Pat. No. 3,242,740. This prior art water sampler system has been proven to have many inherent disadvantages or deficiencies. First, the end of the plastic spout can be contaminated with substances exising at other water depths other than the sampling depth. Hence, contamination of the water sample can occur when the sample is subsequently removed through the spout for analysis. Secondly, the pliable container, with its spout and thick wall elastic container, is expensive to manufacture and is not readily reusable. Third, it has been discovered that the further spreading apart of the plate members at water depths other than the sampling depth has led to some small leakage through the spout sealing mechanism, thereby contaminating the contents of the pliable container. Fourth, the spout, which greatly constricts the entering water flow, can become clogged and some large suspended solids are not collectable since they cannot pass through the spout. Fifth, chemical reagents cannot, on an optional basis, be introduced into the pliable container, since the containers must be provided to the used in a pre-sealed condition. Sixth, the pliable container must be removed from the sampler device, which results in the spout being opened; therefore requiring subsequent resealing of the spout.

U.S. Pat. No. 3,489,012 to Niskin is of interest in disclosing one possible prior art mounting and firing mechanism that can be used in combination with the water sampling device of the present invention.

SUMMARY OF THE INVENTION

The present invention is directed toward a water sampling device having a pliable container or bag which is initially mounted in a deflated condition on a framework. The framework includes sealing means for securing said pliable container with at least a portion of the container in a partially rolled condition to seal an opening in the container. The framework further includes opening means for unrolling the container to expose the opening of the container at the desired water sampling depth. A pair of wing members, which are mounted to the framework, spread apart the sides of the container to draw water through the unsealed opening. After the container has been substantially filled with water, resealing means of the framework rolls the container back up, thereby resealing the container at the sampling depth.

The above-described water sampling device allows for the use of pliable containers of simple construction and design which are inexpensive to manufacture and are readily reusable. Since these containers are received by the user with an opening initially formed therein, chemical reagents, such as sodium thiosulfate, can be introduced into the container prior to sampling. Also, the pre-rolled seal of the container avoids contamination of the area around the container's opening while the container is being lowered to the desired sampling depth. The opening in the container provides a large water passageway which is not readily clogged and which can allow large suspended particles to be collected. The rolled seal formed after the sampling prevents any leakage into the container. Moreover, the latter rolled seal insures an area around the opening which is free of contamination existing at depths other than the sampling depth. The sample in the container can be preserved, shipped, stored and partially prepared for laboratory testing without opening the container.

BRIEF DESCRIPTION OF THE DRAWINGS

Further objects and advantages of the present invention will become apparent as the following description proceeds, taken in conjunction with the accompanying drawings in which.

DETAILED DESCRIPTION OF THE PREFERRED EMBODIMENT

Referring generally to the drawings, there is shown a water sampling device 10 for collecting a water sample in a pliable bag 12 for subsequent analysis. The water sample can be collected in situs in the bag 12 by mounting the bag 12 on a framework 14 which opens, fills and reseals the bag 12. One or more of the water sampling devices 10 can be mounted on a cylindrical holder arrangement, such as that shown in patent 3,489,012 to Niskin, or like mounting and triggering means, and lowered to the desired water depth for obtaining a water sample. The bag 10 is pre-rolled on the framework 14 prior to being introduced into the body of water, thereby insuring a contamination-free area around the opening of the bag 12. The water sampling device 10 is lowered to the desired depth in its completely sealed state so as to prevent contamination from intervening waters. At the desired depth, the bag is unrolled and therefore unsealed, allowing the bag to be directly filled through a mouth or opening 16, which extends along one entire end of the bag 12. This relatively large opening 16 allows suspended solids of substantial size to readily enter the bag 12. After obtaining the sample, the framework 14 quickly reseals the bag 12 by re-rolling the bag at the water depth whereat the water sample was taken. Hence, no contamination of the water sample occurs as the bag is retrieved from the water, removed from the framework 14, and if desired, stored. Hence, the water sampling device 10 can be used, for example, to monitor estuaries, bays, rivers, lakes, reservoirs, ocean outfall sites, as well as performing full ocean depth profiles. The bags 10 insure representative sampling of, for example, suspended solids, waste water, bacteriologic assay, pollutant data, oil spill analysis, and hydrocarbon assays. The sampling device 10 is particularly useful for applications requiring a sterile, non-metalic particle-free container, such as the tightly sealed bag 12.

Figure 1:
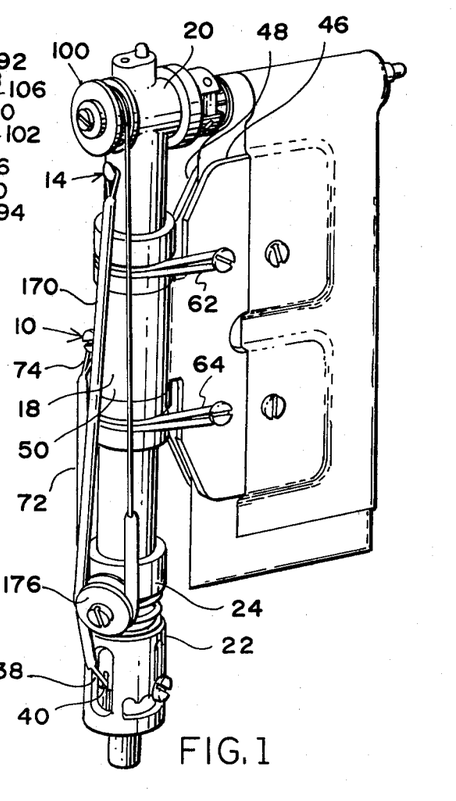
FIG. 1 is a perspective view of the water sampling device of the present invention in its loaded, ready to fire state.
Figure 2:
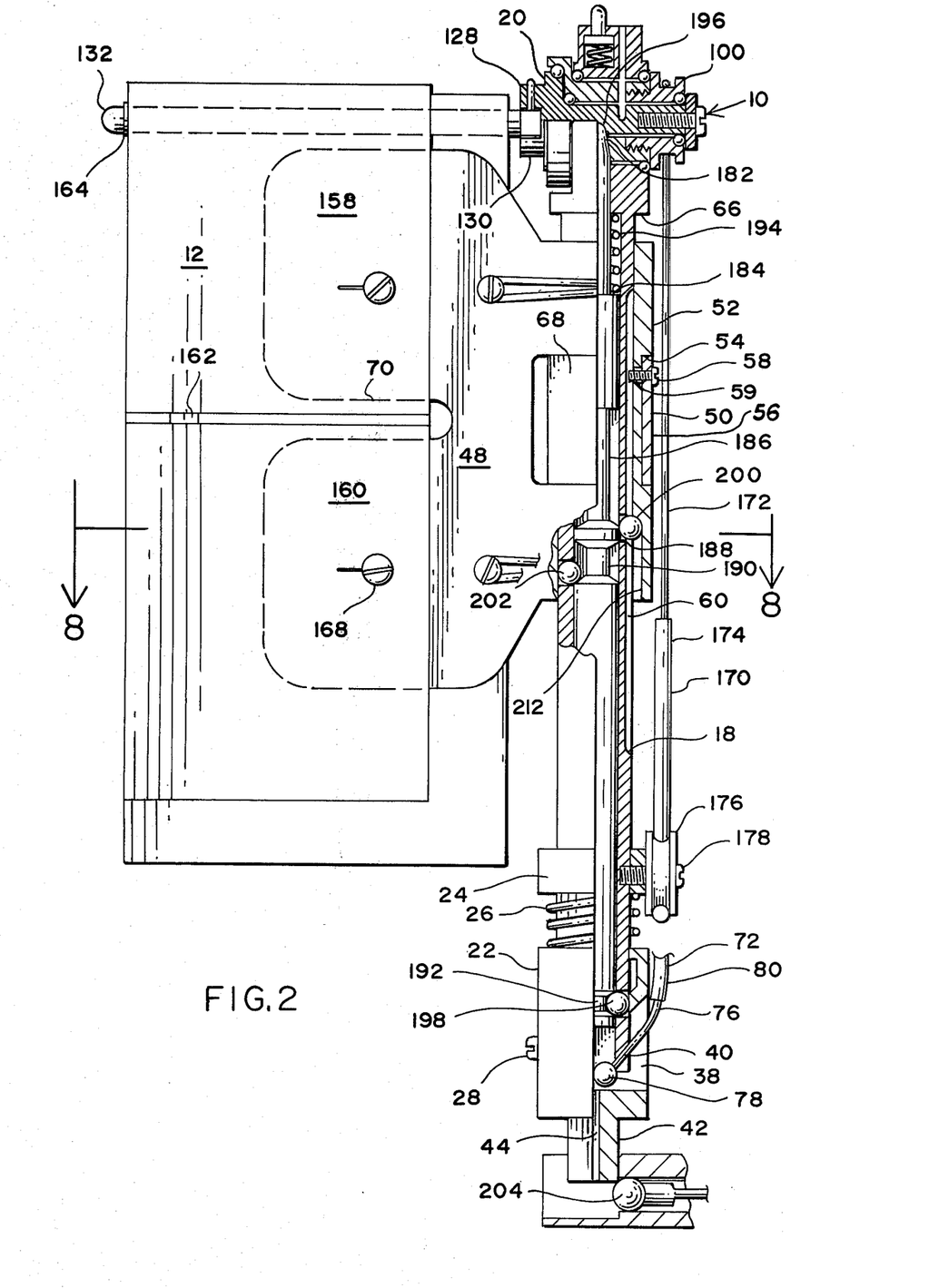
FIG. 2 is a partially broken away side plan view of the sampling device as shown in FIG. 1.
Figure 3:
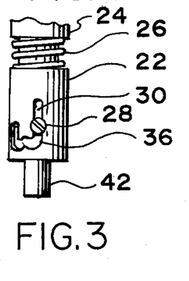
FIG. 3 is an enlarged, fragmentary view of a portion of the sampling device as shown in FIG. 1.

FIGS. 1 through 7 illustrate the sampling device 10 in its loaded, ready for firing state, as will become apparent hereinafter. Referring to FIGS. 1 and 2, the framework 14 comprises a hollow tubular member 18 terminating at one end with a clutch housing 20 and at the opposed end with a slidably secured end sleeve 22. As illustrated in detail in FIGS. 2 and 3, collar stop member 24 is rigidly secured to the tubular member 18 to provide a shoulder against which a coil spring 26 bears, with the other end of the coil spring 26 yieldably urging the end sleeve 22 downward. A removable screw 28 is secured in protruding relationship to the tubular member 18 so as to pass through a j-shaped screw guide 30 formed in the end sleeve 22, thereby providing a stop for the downward urging of the end sleeve 22 caused by the coil spring 26. As depicted in FIG. 3, the j-shaped screw guide 30 has three positions for the screw 28 comprising a ball loading position 32, an intermediately situated mounting position 34, and a firing position 36, which will be described hereinafter. Referring back to FIGS. 1 and 2, an access port 38 is formed in the end sleeve 22 to obtain access to a groove 40 formed in the end of the tubular member 18. A mounting knob 42 depends from the end sleeve 22 and has formed there-through a reloading aperture 44. A pair of first and second plate or wing members 46 and 48 are movably mounted to the tubular member 18 between the clutch housing 20 and the stop collar member 24 by a hinge arrangement 50, which allows for sliding movement of the wing members 46 and 48 along the longitudinal axis of the tubular member 18, while at the same time providing rotational movement of the first wing member 46 about the longitudinal axis of the tubular member 18. The hinge arrangement 50 includes a first sleeve portion 52 disposed for sliding engagement of the tubular member 18. A circular cutout 54 is centrally formed in the first sleeve portion 52 to slidingly hold a second sleeve portion 56. The second sleeve portion 56 has a stop screw 58 rigidly protruding therefrom which passes through an aperture 59 formed in the first sleeve portion 52 and extends into an elongated groove 60 formed in the tubular member 18; thereby preventing the second sleeve portion 56 from rotating. On the other hand, the first sleeve portion 52 is capable of rotation. The first and second wing members 46 and 48 are rigidly attached to the first and second sleeve portions 52 and 56 respectively. Hence, the first wing member 46 can be rotated in one direction toward the second wing member 48 until coming into contact with the second wing member 48 and can be rotated in the other direction away from the wing member 48 until the stop screw 58 engages the vertically disposed side of the aperture 59. A pair of elastic bands 62 and 64 provide a spring bias which, when unrestrained, keeps the wing members 46 and 48 spread apart at their maximum pivotal displacement. Each elastic band 62 and 64 has one end attached to the first wing member 46, wraps around the hinge assembly 50, and attaches at the other end to the second wing member 48. At the same time, when unrestrained, the wing members 46 and 48 can move up and down the tubular member 18, with the collor stop member 24 stopping the downward movement thereof and a shoulder portion 66 of the clutch housing 20 stopping the upward movement thereeof. At least one accurate reinforcing support 68 is provided for each of the wing members 46 and 48 and is attached at one end to the hinge assembly 50 and at the other end to one of the wing members 46 or 48, whereby a more secure attachment of the wing members 46 and 48 is created. Each wing member 46 and 48 has a slot 70 integrally formed therein and extending horizontally from the outer, free edge of the wing member 46 or 48 toward the hinge assembly 50.

Referring to FIGS. 1 and 2, the movement of the wing members 46 and 48 is further controlled by a pull-down spring 72, which terminates at one end with a nylon loop portion 74 secured to the hinge assembly 50, has at the other end a nylon filament portion 76 terminating with an attachment ball 78, and has an elastic center portion 80. When the attachment ball 78 is secured in the groove 40, the pull-down spring 72 provides a yieldable, downward tension on the hinge assembly 50. If unrestrained, the pull-down spring 72 will pull the hinge assembly down against the collar stop member 24.

Figure 4:
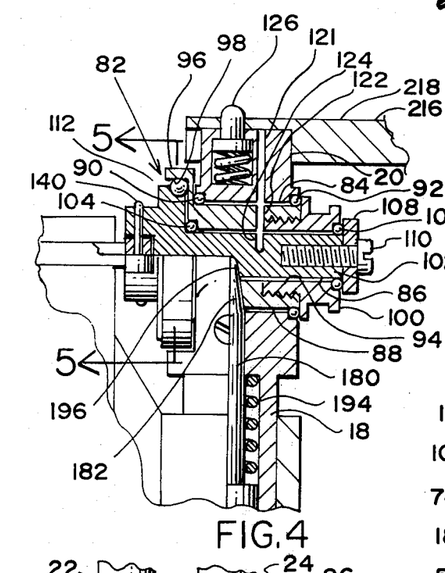
FIG. 4 is an enlarged, fragmentary view of a portion of the sampling device as shown in FIG. 2.

In FIGS. 2 and 4, the clutch housing 20 is partially broken away to illustrate the interior thereof. Referring specifically to the enlarged, fragmentary view of FIG. 4, a clutch assembly 82 is shown wherein a rotatable outer member 84 has a rotatable core member 86 disposed therein. The outer member 84 has an elongated cylindrical portion 88 which is rotatably mounted against the inside surface of the clutch housing 20 by two circular rings of ball bearings 90 and 92 and has an elongated bore 94 formed therein. The outer member 84 further includes an enlarged cylindrical portion 96, with an enlarged bore 98 formed therein, which is integrally attached in coaxial relationship to one end of the elongated cylindrical portion 88. The outer member 84 further includes a clutch pulley 100 which is attached to the end of the elongated cylinder portion 88, which is oppositely disposed to the end having the enlarged cylindrical portion 96. The core member 86 comprises an elongated cylindrical portion 102 which is rotatably mounted inside the elongated bore 94 by two circles of ball bearings 104 and 106. The core member 86 includes a circular cap 108 which is secured to the elongated cylindrical portion 102 by a bolt 110 and which presses against the circle of ball bearings 106. At the opposite end, the core member 86 further includes an integrally formed enlarged cylindrical portion 112 which is disposed in the enlarged bore 98. As described so far, the outer and core members 84 and 86 would be capable of independent rotation with respect to each other; however, the clutch assembly 82 provides for further constraint on the members' movement as shown in detail in the cross-sectional view of FIG. 5. The inner wall 114 of the enlarged cylindrical portion 96 has three gradually decreasing slots 116 formed therein, with one ball bearing 118 mounted in each slot 116. Hence, with respect to FIG. 5, the core member 86 can rotate free of the outer member 84 in a counterclockwise direction, but when rotated in a clockwise direction, the members 84 and 86 are locked together and therefore rotate as a single unit. Referring back to FIG. 4, the ball bearings 118 are maintained between the members 84 and 86 by a circular ledge 120.

As depicted in FIG. 4, slots 121, 122 and 124 are formed respectively in the clutch housing 20, the outer member 84 and the core member 86. When these slots are vertically aligned, as shown in FIG. 4, a pin (not shown) can be inserted into the slots; thereby locking the outer and core members 84 and 86 in a stationary position with respect to the clutch housing 20. A depressable, spring biased mounting prong 126 is positioned at the top of the clutch housing 20.

Figures 5, 7, 9:
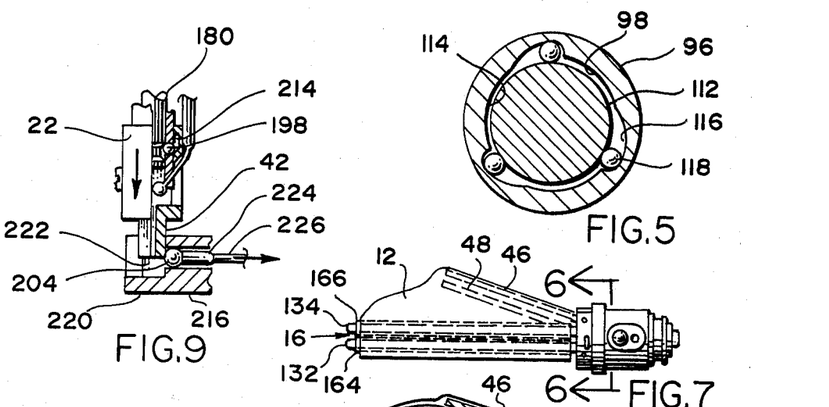
FIG. 5 is a cross-sectional view of the sampling device taken with respect to section line 5—5 in FIG. 4.
FIG. 7 is a top plan view of the sampling device as shown in FIG. 2.
FIG. 9 is a fragmentary view of a portion of the sampling device just after the sampling device has been fired.
Figures 6, 11, 12, 13, 15:
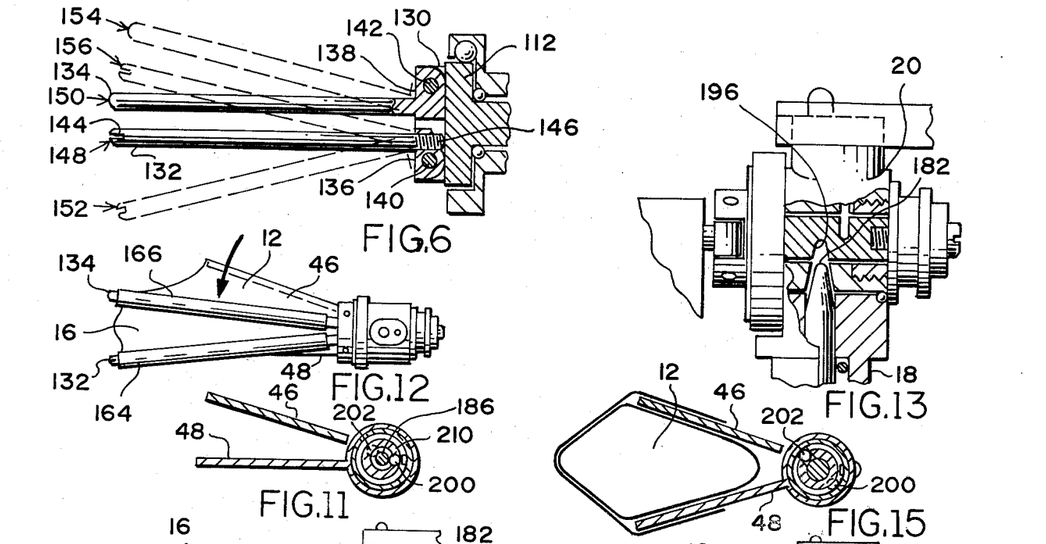
FIG. 6 is a cross-sectional view of the sampling device taken with respect to section line 6—6 in FIG. 7.
FIG. 11 is a cross-sectional view of the sampling device taken with respect to section line 11—11 in FIG. 10.
FIG. 12 is a top, plan view of the sampling device as shown in FIG. 10.
FIG. 13 is a further broken away, fragmentary, enlarged view of a portion of the sampling device as shown in FIG. 10.
FIG. 15 is a cross-sectional view of the sampling device taken with respect to section line 15—15 in FIG. 14.

Referring to FIGS. 2 and 6, the enlarged cylindrical portion 112 has a pair of spaced apart protruding ledges 128 and 130 integrally formed thereon for mounting a pair of rods 132 and 134. The rods 132 and 134 each terminate in a mounting block 136 and 138, respectively, which are pivotally attached to the ledges 128 and 130 by a pair of pins 140 and 142, respectively. Rotation of the rod 132, by use of end slot 144, allows for varying the extention of a threaded end 146 of the rod 132 through the mounting block 136. The rods 132 and 134 have a parallel position at 148 and 150, respectively, and a pivoted outward position at 152 and 154, respectively. However, when the rod 132 is threaded so as to be flush with the inner surface of the mounting block 136, it can swing to a second parallel position at 156. Consequently, with respect to FIG. 5, the rods 132 and 134 are capable of rotating outward together in a clockwise direction. It is contemplated that two flexible, plastic rods, which are rigidly attached to the enlarged cylindrical portion 112, can be used in place of the rigid rods 132 and 134, which are typically formed of metal.

Referring to FIGS. 2 and 7, the bag 12 is made of a sheet of pliable material, such as Teflon or a polyethylene, with each edge, except the edge defining the opening 16, being sealed. The bag is provided with two pairs of pockets 158 and 160, one pair being on each side of the bag. Each pair of pockets is formed by sealing an outer sheet of plastic to the bag 12, securing it at the top and bottom, and forming a seam 162 in the middle. Hence, the seam 162 will be slide along slot 70 of the wing members 46 and 48 when the bag is mounted. A pair of straw-like tubes are secured to the top edges of the bag, adjacent the opening 16, each tube being mounted for receiving one of the rods 132 and 134. When the bag 12 is mounted, each wing 46 and 48 is secured in protruding relationship in one of the pairs of pockets 158 and 160 by screws 168. In loading the bag 12, the tubes 164 and 166 are slipped over the rods 132 and 134. Then the bag 12 is wrapped in a counterclockwise direction for approximately two complete rolls, with the wings 46 and 48 being subsequently positioned in the pockets 158 and 160, as better shown in FIG. 1. When the sampling device 10 is in its loaded, ready for firing state, the bag 12 with be deflated.

Referring to FIGS. 1 and 2, a wind-up spring 170, having a filament portion 172 and an elastic portion 174 is attached to the clutch housing 20 at one end and then is looped around a lower pulley 176, which is mounted to the collar stop member 24 by a bolt 178. In its loaded, ready to fire state, the filament portion 172 is wrapped around the clutch pulley 100. More specifically, the filament portion 172 is wrapped around the clutch pulley 100 in a direction that will rotate, when unrestrained, the outer member 84 and the core member 86 as one unit; thereby making use of the one-way latching effect of the ball bearings 118.

Referring to FIG. 2, a shaft 180 is configured and dimensioned to slide within the interior of the tubular member 18, when unrestrained. The shaft 180 has a tapered end portion 182, a shoulder portion 184, a first cut-out portion 186, a collar portion 188, a second cut-out portion 190 and a circular groove portion 192. A coil spring 194 provides a downwardly directed spring pressure, which is applied to the shoulder portion 184. When the sampling device 10 is in its loaded, ready to fire state, the end portion 182 extends upward into a slot 196 formed in the outer member 84 and the core member 86; thereby locking them into stationary positions and preventing rotation. The steps for achieving this loaded state will be described hereinafter. The vertical displacement of the shaft 180, which when loaded is urged downward by the coil spring 194, is controlled by a first control ball 198 and a second control ball 200. The position of the first wing 46 with respect to the second wing 48 is controlled by a third control ball 202. A control knob 204 controls the vertical displacement of the end sleeve 22.

Figure 8:
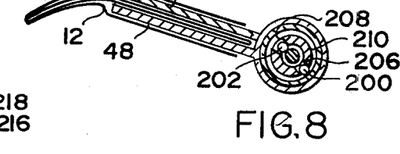
FIG. 8 is a cross-sectional view of the sampling device taken with respect to section line 8—8 in FIG. 2.

Referring to FIGS. 2 and 8, the second control ball 200 and third control ball 202 extend into a first orifice 206 and a second orifice 208, respectively, each of which are formed in the tubular member 18. Depending on the vertical elevation of the shaft 180, the collar portion 188 can engage the control balls 206 and 208, causing them to extend past the outer periphery 210 of the tubular member 18. A vertically aligned elongated slot 212 is formed on the inside of the first sleeve portion 52 and extends from the bottom thereof up to a point short of the second sleeve portion 56. When the slot 212 is aligned with the second control ball 200, the second ball 200 can extend beyond the periphery 210 of the tubular member 18. A vertically aligned groove 230, as shown in later described FIGURES, is formed in the first sleeve portion 52 to receive the second control ball 200.

Referring to FIGS. 2 and 9, an enlarged view of the end of the sampling device 10 is illustrated in FIG. 9. When the end sleeve 22 is lowered, the first control ball 198 can slip partially into an undercut 214 formed in the end sleeve 22. A mounting and firing mechanism 216, preferably in the form of that illustrated in U.S. Pat. No. 3,489,012 to Niskin, is partially shown. The upper end of the water sampling device 10 is removably mounted by the compressable mounting prong 126 into a first bracket 218 of mechanism 216, as shown in FIG. 4. Referring back to FIGS. 2 and 9, the lower end of the water sampling device 10 is detachably secured in a second bracket 220 of the mechanism 216 by the mounting knob 42. The second bracket 220 is held in a cavity 222 which opens into a channel 224. The control knob 204, which is operatively connected to a retractable rod 226 is situated in the channel 224 for retractable movement away from the mounting knob 42. As can be appreciated by those skilled in the art, the mechanism 216 can take many different forms and can be used to mount one or more water sampling devices 10. There is commercially available from General Oceanics, Inc. of Miami, Fla. a mechanism 216 wherein up to 24 water sampling devices 10 can be mounted. The unit is available either as a programable, self-powered unit or as an operator controlled unit. For example, the unit can be programmed to sample over a period of several hours at a given site, or alternatively, it can sample at different depths. The specific structure of the mechanism 216 is per se not part of the present invention.

The operation of the sampling device 10 will now be described in detail. The sampling device 10 is depicted in its loaded, ready to fire state in FIGS. 1 through 8. The sampling device 10 is in this state after it is mounted in the mechanism 216. Thereafter, the sampling device 10 is lowered into the water to the desired depth at which the water sample is to be taken. Referring to FIG. 2 in particular, the bag 12 has been mounted so that the rods 132 and 134 are positioned inside the tubes 164 and 166, the bag 12 is wrapped around the rods 132 and 134, and the pockets 158 and 160 for each side of the bag 12 are slipped over the wing members 46 and 48. The shaft 180 is positioned at its highest possible elevation, with the tapered end 182 securely locking the outer and core members 84 and 86, thereby preventing rotation thereof. The shaft 180 is maintained in its upward elevation by the first control ball 198, which is biased inward by the end sleeve 22 so as to be inserted into the groove portion 192. The positioning of the end sleeve 22 to accomplish this biasing is implemented by resting the mounting knob 42 on the control knob 204, which is initially positioned to extend into the cavity 222, thereby maintaining the end sleeve 22 in its elevated position. The wing members 46 and 48 are positioned adjacent the clutch housing 20, with the first sleeve portion 52 preferably being slightly spaced apart from the shoulder portion 66. The first wing member is rotated inward so as to be closely positioned adjacent to the second wing member 48, thereby allowing the bag 12 to be in a deflated condition. With the relative positioning of the shaft 180, the tubular member 18 and the wing members 46 and 48, the second and third control balls 200 and 202 are disposed as shown in FIGS. 2 and 8. The collar portion 188 securely maintains the second control ball 200 in its outward protruding disposition so as to be inserted in the elongated slot 212; counteracting the biasing force of the elastic bands 62 and 64 so as to thereby prevent the first wing member 46 from rotating outward from the second wing member 48. Also, the control ball 200 prevents the wing members 46 and 48 from moving downward along the tubular member 18, and thereby counterbalances the downward tension of the pull-down spring 72. However, at the time of the mounting of the bag 12, the wing members 46 and 48 can slide upward until the first sleeve portion 52 engages the shoulder portion 66, due to the length of the elongated slot 212. Hence, the mounting of the bag 12 is made easier. The third control ball 202 is disposed in its inwardly protruding position so as to extend into the second cut-out portion 190. The third control ball 202 is maintained in this position by the abutting relationship of the inner surface of the first sleeve portion 52.

Referring to FIG. 9, the sampling device 10 is activated or fired by the mechanism 216 retracting the control knob 204, which in turn allows the spring biased end sleeve 22 to spring downward. The device 10 is fired at a water depth and/or time at which a water sample is desired. FIG. 9 shows the end sleeve 22 in a position achieved just after the retraction of the control knob 204. As the end sleeve 22 moves down, the first control ball 198 slips out of the groove 192 into the undercut 214; thereby allowing the shaft 180 to drop.

Figure 10:
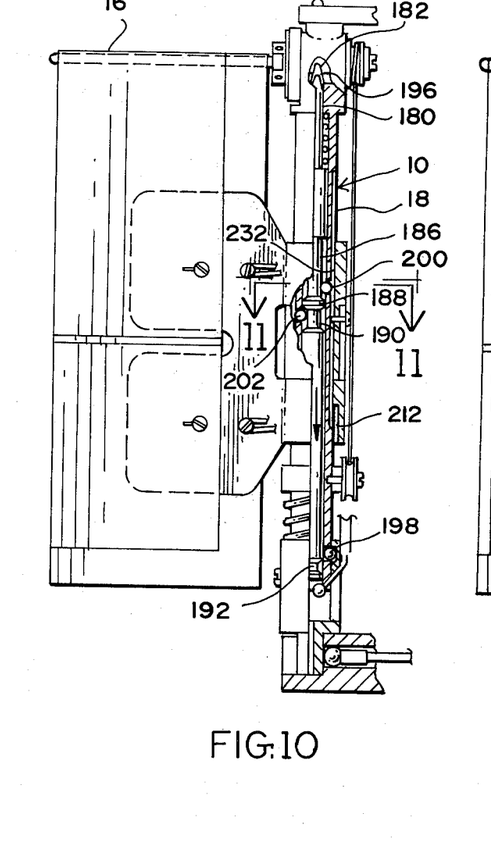
FIG. 10 is a broken away, side view of the sampling device after it has been fired and the wing members have descended.

FIGS. 10, 11, 12 and 13 illustrate the next step of the automatic operation of the sampling device 10, which is the opening of the bag 12. After the first ball releases the shaft 180, the downward movement of the collar portion 188 releases the second control ball 200, so that it pops into the first cut-out portion 186; thereby freeing the first sleeve portion 52 for outward rotational movement. At the same time, the downward displacement of the tapered point 182, frees the core member 86 for rotation about its center axis. The pull-down spring 72 pulls the wing members 46 and 48 downward until the core member 86, with its protruding rods 132 and 134, has rotated sufficiently to completely unroll the bag. The downward movement of the wing members 46 and 48 will stop when the bag 12 is completely stretched out with its opening 16 exposed to the surrounding water. In this stationary, open state, the lower edge of the first sleeve portion 52 is disposed in space-apart adjacent relationship with respect to the collar stop member 24. Also, when the second control ball 200 moves out of the elongated slot 212, the spring biased first wing member 46 rotates outward from the second wing member 48. As the wing members 46 and 48 spread apart, the sides of the bag 12 spread apart, thereby sucking the water sample into the bag 12 through the opening 16. Since the rods 132 and 134 are pivotally mounted, they likewise spread apart to provide for a large opening 16, as shown in FIG. 12. The shaft 180 will continue to drop until the collar portion 188 engages the inward protruding third control ball 202. This holds the shaft 180 in its second intermediate elevation while the wing members 46 and 48 are rotating apart. In FIGS. 10, 11 and 12 the wing members 46 and 48 are shown partially opened, as the water is filling the bag 12. During this time, as shown in particular in FIG. 11, both control balls 200 and 202 are disposed flush with the outer periphery 210 of the tubular member 18, due to their being retained within the periphery 210 by the inner wall 232 of the first sleeve portion 52.

Figure 14:
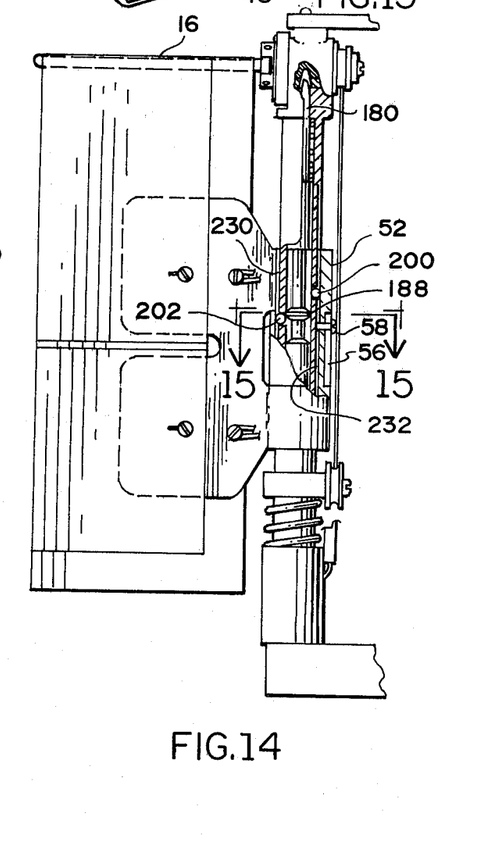
FIG. 14 is a partially broken away side view of the sampling device after the wing members have spread apart.
Figure 16:
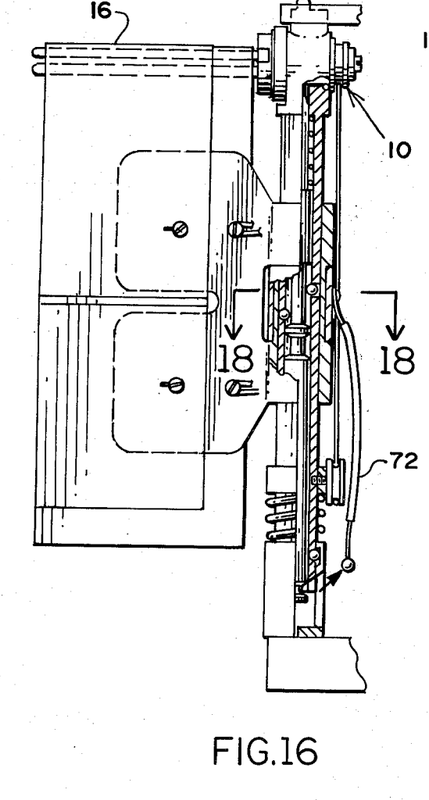
FIG. 16 is a partially broken away side view of the sampling device as the wing members are moving upward.

Referring to FIGS. 14 and 15, as the bag 12 fills, the wing members 46 and 48 rotate apart, as particularily shown in FIG. 15. The bag 12 itself limits the amount of rotation or opening of the wing member 52. The stop created by the screw 58 hitting the edge of sleeve portion 56 is needed only when the filled bag 12 is removed. At this point, the third control ball 202 is aligned with the vertically disposed groove 230, which is formed in the inner wall 232. Hence, this rotational alignment allows for the shaft 180 to move without interference pass the control ball 202. Due to the spring biasing of the shaft 180, the collar portion 188 pushes the control ball 202 into the groove 230, which in turn allows the shaft 180 to drop further to a third position which is its lowest elevation.

Figures 17, 19:
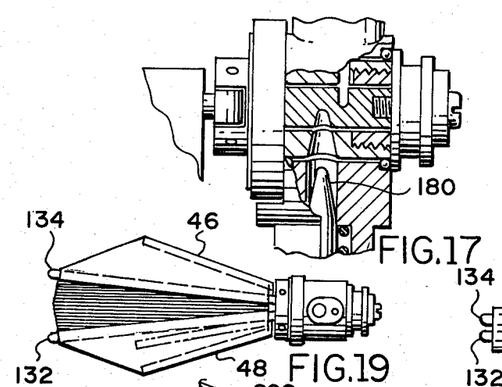
FIG. 17 is a further broken away, enlarged fragmentary view of a portion of the sampling device as shown in FIG. 16.
FIG. 19 is a top plan view of the sampling device as shown in FIG. 16.
Figure 18:
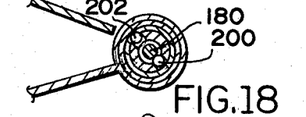
FIG. 18 is a cross-sectional view of the sampling device taken with respect to section line 18—18 in FIG. 16.

In FIGS. 16, 17, 18 and 19, the shaft 180 is shown at its lowest elevation. As the shaft 180 proceeds downward, the lower end of the shaft 180 strikes the attachment ball 78 so as to disengage the same from its groove 40; thereby eliminating the downward tension on the hinge assembly 50 which was created by the pull-down spring 72. At approximately the same moment, as shown by FIG. 17, the downward displacement of the tapered point 182 frees the outer member 84 for rotation about its center axis. Prior to the shaft 180 dropping to its lowest elevation, the only force counteracting the tension force of the wind-up spring 170, which is wrapped several times around the pulley 100, were the rotational stop provided by the tapered point 182 and the downward tension of the pull-down spring 72. Consequently, the wind-up spring 170 now rotates the outer member 84, and due to the clutching action, the core member 86. Consequently, the bag 12 is rolled up in a direction opposite to the direction in which it was initially rolled, prior to firing. The rolling of the bag 12 creates a water-tight seal. As the rewinding action is initiated, the shaft 180 remains stationary at its lowest elevation. On the other hand, the wing members 46 and 48 are pulled upward by the rolling of the bag 12. The groove 230 vertically extends along the entire vertical length of the inner wall 232. As will become apparent hereinafter, this groove 230 allows for a more simplified reloading procedure. In FIG. 18, the wing members 46 and 48 have moved up only part of the final distance.

Figure 20:
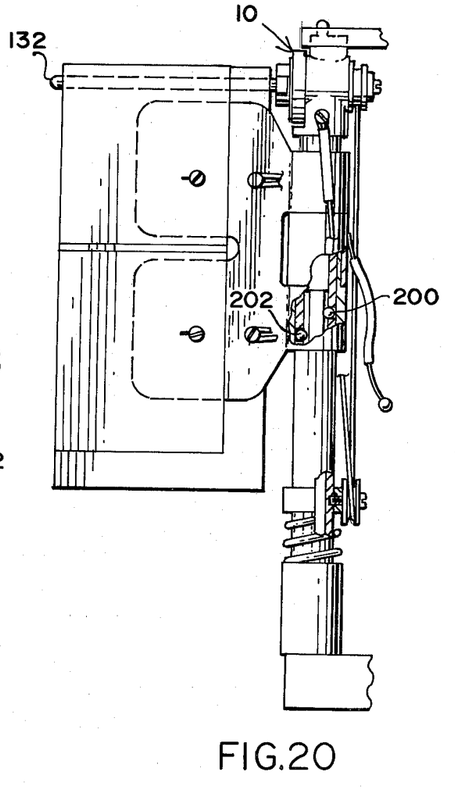
FIG. 20 is a partially broken away side view of the sampling device after the bag has been resealed.
Figure 21:
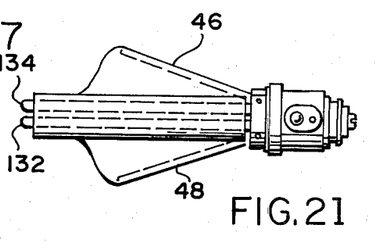
FIG. 21 is a top, plan view of the sampling device as shown in FIG. 20.
Figure 22:
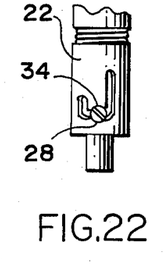
FIG. 22 is a fragmentary view of a portion of the sampling device as it is being mounted.

In FIGS. 20 and 21 the bag 12 is shown as being completely rolled up. The rolling of the bag about the rods 132 and 134, pivots them back in their relatively parallel positions, as shown in FIG. 22. After the bag 12 has been sealed, the sampling device 10 is raised to the surface and the bag 12 is removed. The screws 168 are removed, the bag is manually grasped at the outer tip of the rolled seal. Then the bag is pulled off the framework 14. Clips (not shown) can be used to keep the bag 12 sealed.

The sampling device 10 can now be reloaded for subsequent reuse by primarily reversing most of the heretofore described mechanical steps. The wind-up spring 170 and the pull-down spring 72 are loosened. A cotter key (not shown) is inserted into slot 121 and the outer and core members 84 and 86 are rotated while manually applying light pressure, so that the cotter key passes through all three slots 121, 122 and 124. This provides the proper alignment of these three elements. Then the framework 14 is inverted, and pressed against a supporting structure, such as a table, with the cotter key remaining in place. A loading rod (not shown) is inserted through the reloading aperture 44. The wing members 46 and 48 are allowed to slide freely and are allowed to fall against the shoulder portion 66 of the clutch housing 20. The loading rod is manually pressed down firmly until it will go no further. This causes the collar portion 188 to push the third control ball 202 into the groove 230; which in turn allows the collar portion 188 to move past the ball 202. Then the wing members 46 and 48 are pressed together, and once again the loading rod is manually pressed down upon, until it stops. The collar portion 188 has then pushed the second control ball 200 into the elongated slot 212. Hence, the wing members 46 and 48 remain closed if now released. While maintaining full pressure on the loading rod, the end sleeve 22 is manually forced downward and rotated until the screw 28 moves into the ball loading position 32 of the end sleeve 22, as shown in FIG. 3. This locks the first control ball 198 into the groove 192. The cotter pin and loading rod are now removed. With the framework 14 in its upward position, the filament portion 172 is wound clockwise four turns about the clutch pulley 100. The end of the wind-up spring 170 is attached to the clutch housing 20 and then the wind-up spring 170 is wrapped around the pulley 176. The attachment ball 78 of the pull-down spring 72 is inserted into the groove 40. The end sleeve 22 is manually depressed and rotated until the screw 28 is secured in the mounting position 34 of the end sleeve 22. Next, the bag 12 is attached in the following described manner. The slotted rod 132 is unscrewed, and the rods 132 and 134 are pivoted outward to their positions 152 and 154, shown in FIG. 6, so that the rods 132 and 134 are positioned over the closed wing members 46 and 48. With the bag 12 partially rolled, the tubes 164 and 166 of the bag 12 are slid over the rods 132 and 134. The free end of the bag 12 is swung downward and slipped between the wing members 46 and 48, while the wing members are slid into the pockets 158 and 160 on each side of the bag 12. The screws 168 are attached to securely retain the bag 12. A screwdriver (not shown) is inserted into end slot 144 of the rod 132, and the rod 132 is screwed inward until the rods 132 and 134 assume their positions 148 and 150, respectively, as shown in FIG. 6. Next, the sampling device 10 is mounted between the brackets 218 and 220 by snapping it into place. Finally, the end sleeve 22 is rotated until the screw 28 is positioned in the firing position 36, as shown in FIG. 3. Although a loading rod is used to reposition the shaft 180, it is contemplated that the mounting knob 42 can be constructed so as to be a depressable button that could be pushed up to reposition the shaft 180.

Although particular embodiments of the invention have been shown and described here, there is no intention to thereby limit the invention to the details of such embodiments. On the contrary, the invention is to cover all modifications, alternatives, embodiments, usages and equivalents of the subject invention as fall within the spirit and scope of the invention, specification and the appended claims.

What is claimed is:

1. In a water sampling device having a pliable container, with an initially sealed opening, mounted in a deflated condition on a framework and means for spreading apart the sides of said pliable container to draw water through said opening when unsealed, the improvement comprising:

said framework including sealing means for securing said pliable container in at least a partially rolled condition to seal said opening;

said framework further including opening means for unrolling said pliable container to expose said opening;

said framework further including resealing means for rolling said pliable container to reseal said opening after said means for spreading apart the sides of said pliable container has substantially filled said pliable container with water.

2. The water sampling device according to claim 1 wherein said pliable container has a pair of sidewalls with said sidewalls defining said opening at one end of said pliable container, said means for spreading apart the sides of said pliable container include a pair of wing members, with one said wing member being attached to one of said sidewalls and the other said wing member being attached to said other sidewall and further includes means for pivotally swinging at least one of said wing members in a direction away from said other wing member.

3. The water sampling device according to claim 2 wherein said framework includes a pair of rods, one said rod being attached to one said sidewall adjacent said opening and the other said rod being attached to the other said sidewall adjacent said opening, said rods being adapted to have at least a portion of said pliable container initially rolled around said rods, said framework further including means for simultaneously rotating said rods to unroll said pliable container so as to expose said opening and to roll said pliable container to reseal said opening.

4. In a water sampling device having a pliable container, with a pair of sidewalls and an initially sealed opening, and a pair of wing members attached to said sidewalls and operative to spread apart said sidewalls from an initially deflated condition to allow water to substantially fill said pliable container through said opening, the improvement comprising:
   a pair of rods attached to said pliable container adjacent said opening with one said rod being attached to one said sidewall and the other said rod being attached to said other sidewall, said rods being adapted to have at least a portion of said pliable container initially rolled around said rods;
   a clutch assembly having a rotatable outer member operative to rotate in either direction about a center axis of said clutch assembly, a rotatable core member operative for rotational movement with respect to said rotatable outer member in one direction about said center axis and operative to lockingly engage said rotatable outer member when rotated in the other direction, said rods being attached to said rotatable core member;
   stop means for initially locking said rotatable outer member and said rotatable core member in stationary, locked positions;
   opening means for releasing said rotatable core member from said locked position and for moving said wing members in a direction away from said rods until said pliable container is unrolled and said opening is exposed;
   resealing means for rotating said rotatable outer member in a direction that lockingly engages said rotatable core member to roll said pliable container about said rods after said pliable container has been substantially filled with water.

5. In a water sampling device having a pliable container, with a pair of sidewalls and an initially sealed opening, and a pair of wing members attached to said sidewalls and operative to spread apart said sidewalls from an initially deflated condition to allow water to substantially fill said pliable container through said opening, the improvement comprising:
   a pair of rods attached to said pliable container adjacent said opening with one said rod being attached to one said sidewall and the other said rod being attached to said other sidewall, at least a portion of said pliable container being initially rolled around said rods;
   a clutch assembly having a rotatable outer member operative to rotate in either direction about a center axis of said clutch assembly, a rotatable core member operative for rotational movement with respect to said rotatable outer member in one direction about said center axis and operative to lockingly engage said rotatable outer member when rotated in the other direction, said rods being attached to said rotatable core member;
   a tubular member having said clutch assembly mounted at one end of said tubular member and having a longitudinal axis being disposed in substantially perpendicular relationship to said center axis of said clutch assembly, said wing members being mounted on said tubular member for sliding movement with respect to said longitudinal axis of said tubular member, said wing members being initially positioned in close proximity to said clutch assembly, at least one of said wing members being pivotally mounted to said tubular member for pivotal rotation about said longitudinal axis;
   a first biasing means for yieldably urging said wing members in a direction away from each other;
   a second biasing means for yieldably urging said wing members in a direction away from said clutch assembly;
   a third biasing means for yieldably urging said outer rotatable member to rotate about said center axis in the direction which lockingly engages said rotatable core member;
   control means including first stop means for initially locking said rotatable outer member and said rotatable core member in stationary, locked positions and a second stop means for initially locking said pivotally mounted wing member in close proximity relationship to the other said wing member;
   said control means further including first release means for releasing said rotatable outer member from said locked position, whereby said second biasing means pulls said wing member in a direction away from said clutch assembly, thereby unrolling said pliable container, and exposing said opening;
   said control means further including second release means for releasing said pivotally mounted wing member from said close proximity relationship with said other wing member, whereby said first biasing means rotates said pivotally mounted wing member;
   said control means further including third release means for releasing said rotatable outer member from said locked position when said pivotally mounted wing member has swung to a predetermined position, whereby said third biasing means rolls up said pliable container.

6. The water sampling device according to claim 5, wherein said control means comprises a shaft positioned for sliding displacement inside of said tubular member, means for yieldably urging said shaft in a direction away from said clutch assembly, said shaft having three operative elevations comprising an upper elevation, an intermediate elevation, and a lower elevation.

7. The water sampling device according to claim 6, wherein said first stop means comprises said shaft initially being disposed in said upper elevation with an upper end of said shaft protruding through said rotatable outer member into said rotatable core member and a first control ball movably mounted in said tubular member and disposed to lockingly engage said shaft to maintain said shaft in said upper elevation, said second stop means comprises a second control ball movably mounted in said tubular member and disposed to lock in place said pivotally mounted wing member when said shaft is in said upper elevation.

8. The water sampling device according to claim 7, wherein said first stop means further comprises an end sleeve movably mounted in surrounding relationship to the end of said tubular member opposite said end having said clutch assembly, said end sleeve having a first position for biasing said first control ball to lock in place said shaft and a second position for releasing said first control ball from its locking relationship with said shaft, said second stop means comprises a collar portion formed on said shaft, said collar portion disposed to engage said second control ball to lock in place said wing members when said shaft is in said upper elevation.

9. The water sampling device according to claim 8, wherein said first release means comprises means for moving said end sleeve to said second position whereby said first control ball releases said shaft so that said shaft moves to said intermediate elevation, said shaft being stopped at said intermediate elevation by said shaft engaging a third control ball which is movably mounted in said tubular member, said rotatable core member being released for rotational movement when said shaft is in said intermediate position.

10. The water sampling device according to claim 9, wherein said second release means comprises said collar portion of said shaft being operative to release said second control ball from its locking relationship with said wing members when said shaft is in said intermediate position, whereby said wing members spread apart.

11. The water sampling device according to claim 10, wherein said third release means comprises means for releasing said third control ball from its stopping engagement with said shaft when said wing members have swung to said predetermined position.

12. The water sampling device according to claim 11 wherein each said wing member has a sleeve portion for mounting said wing member to said tubular member, said sleeve portion of said pivotally mounted wing member having a groove formed therein, said groove being aligned to release said third control ball when said wing member is in said predetermined position.

* * * * *